United States Patent [19]
Guillaumet et al.

[11] Patent Number: 5,242,923
[45] Date of Patent: Sep. 7, 1993

[54] 3-AMINO-2-HYDROXYPYRIDINE

[75] Inventors: Gérald Guillaumet, Orleans; Christine Flouzat, Clermont Ferrand; Michelle Devissaguet, Neuilly Sur Seine; Pierre Renard, Versailles; Daniel H. Caignard, Paris; Gérard Adam, Le Mesnil Le Roi, all of France

[73] Assignee: Adir Et Compagnie, Courbevoie, France

[21] Appl. No.: 839,819

[22] Filed: Feb. 21, 1992

Related U.S. Application Data

[62] Division of Ser. No. 792,423, Nov. 15, 1991, Pat. No. 5,130,311.

[30] Foreign Application Priority Data

Nov. 20, 1990 [FR] France ................... 90 14381

[51] Int. Cl.$^5$ ................... A61K 31/495; C07D 401/00
[52] U.S. Cl. ................... 514/252; 544/360
[58] Field of Search ................... 544/360; 514/252

[56] References Cited

U.S. PATENT DOCUMENTS

| | | | |
|---|---|---|---|
| 3,929,809 | 12/1975 | Kristinsson et al. | 546/116 |
| 5,061,713 | 10/1991 | Guillaumet et al. | 514/302 |
| 5,084,456 | 1/1992 | Guillaumet et al. | 514/252 |

FOREIGN PATENT DOCUMENTS 412899  2/1991  European Pat. Off. ............ 544/360

*Primary Examiner*—Cecilia Tsang
*Attorney, Agent, or Firm*—Gordon W. Hueschen

[57] ABSTRACT

The invention relates to the compounds of general formula (I):

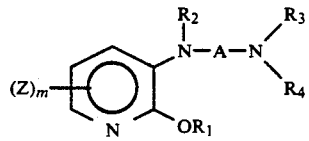

in which:

$R_1$, $R_2$, $R_3$, $R_4$, A, Z and m are as defined in the description, their isomers, epimers and diastereoisomers, their addition salts with a pharmaceutically acceptable acid and, when $R_1$ and $R_2$ each represent a hydrogen atom, their addition salts with a pharmaceutically acceptable base.

6 Claims, No Drawings

3-AMINO-2-HYDROXYPYRIDINE

This application is a divisional application of Ser. No. 07/792,423, filed Nov. 15, 1991, now U.S. Pat. No. 5,130,311.

The present invention relates to new oxazolo[5,4-b]pyridine compounds, to processes for preparing these and to pharmaceutical compositions containing them.

The properties, both analgesic and anti-inflammatory, of 2-phenyloxazolo[5,4]-or -[4,5]pyridines are already known (Patents U.S. Pat. No. 4,038,396, FR 2,328,471, FR 2,319,354, GB 1,421,619, U.S. Pat. No. 232,740).

However, these compounds possess an essentially anti-inflammatory profile, as confirmed by the therapeutic indications mentioned in the patents cited above, or else have the drawback of not dissociating the two types of activity: analgesic on the one hand, anti-pyretic and anti-flammatory on the other hand.

The new compounds discovered by the Applicant possess not only a level of analgesic activity at least equivalent to that of the already known 2-phenyl-3H-oxazolo[4,5-b]- or -[5,4-b]pyridines, but also possess the very advantageous feature of being virtually devoid of anti-inflammatory effects.

Most non-morphinic analgesic substances known to date also possess anti-inflammatory activity and hence intervene in the processes linked to the phenomena of inflammation (this is the case, for example, with salicylate compounds such as aspirin, pyrazoles such as phenylbutazone, arylacetic or heteroarylacetic acids such as indomethacin, etc.). Being anti-inflammatory, these substances inhibit cyclooxygenase, thereby causing a blockade of the biosynthesis of numerous chemical mediators (prostaglandins, prostacyclin, thromboxane A2, etc.). Multifarious side-effects hence ensue, including inhibition of platelet aggregation associated with disorders of coagulation, and a gastrointestinal toxicity with the possibility of ulcerations and of hemorrhage due to a decrease in the biosynthesis of prostaglandins PG $E_2$ and PG $F_1$ α which are cytoprotective of the gastric mucosa.

Apart from the problems they cause, these side-effects can, in many subjects who are especially sensitive to them, make it impossible to prescribe substances endowed with anti-inflammatory properties.

Since the compounds of the present invention do not interact with the mediators of inflammation, they are hence devoid of the side-effects mentioned above.

This feature, combined with their absence of toxicity and their high level of activity, renders the compounds of the present invention usable as analgesics without the restrictions on their use which normally apply to the majority of the products of this class.

More specifically, the invention relates to the compounds of general formula (I):

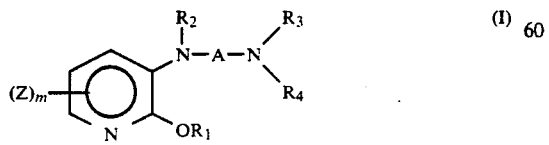

in which:
$R_1$ and $R_2$ each represent a hydrogen atom or, with the oxygen and the nitrogen which carry them, form an —O—CO—N— linkage, corresponding to oxazolo[5,4-b]pyridin-2-ones, Z represents halogen, linear or branched lower alkyl comprising from 1 to 6 carbon atoms, linear or branched lower alkoxy comprising from 1 to 6 carbon atoms or trifluoromethyl, m is an integer which can take the values 0, 1, 2, 3, A is a linear or branched alkyl radical comprising from 1 to 6 carbon atoms, $R_3$ and $R_4$, which may be identical or different, represent:
hydrogen,
linear or branched lower alkyl comprising from 1 to 6 carbon atoms,
linear or branched lower alkenyl comprising from 1 to 6 carbon atoms,
optionally substituted aryl or heteroaryl,
optionally substituted arylalkyl or heteroarylalkyl in which the alkyl chain comprises from 1 to 3 carbon atoms,
mono- or bicyclic cycloalkyl having 3 to 10 carbon atoms, or alternatively:
$R_3$ and $R_4$, with the nitrogen atom to which they are linked, constitute a saturated or unsaturated, mono- or bicyclic, nitrogenous heterocyclic system comprising not more than 12 atoms, not counting the hydrogen atoms, which can include from one to three hetero atoms chosen from nitrogen, oxygen or sulfur, and optionally substituted with one or more:
hydroxyl,
oxo,
linear or branched lower alkyl comprising from 1 to 6 carbon atoms,
optionally substituted aryl,
optionally substituted arylalkyl or optionally substituted diarylalkyl in which the alkyl chain contains from 1 to 3 carbon atoms,

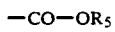

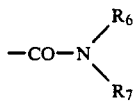

$R_5$ represents:
hydrogen,
linear or branched lower alkyl comprising from 1 to 6 carbon atoms,
optionally substituted aryl,
optionally substituted aralkyl in which the alkyl chain comprises from 1 to 3 carbon atoms, $R_6$ and $R_7$, which may be identical or different, have the same meaning as $R_5$,
their isomers, epimers and diastereoisomers,
their addition salts with a pharmaceutically acceptable acid and/or, when $R_1$ and $R_2$ each represent a hydrogen atom, their addition salts with a pharmaceutically acceptable base,
aryl group being understood to mean an unsaturated or aromatic, mono- or bicyclic group comprising from 5 to 12 carbon atoms,
heteroaryl group being understood to mean an unsaturated or aromatic, mono- or bicyclic group comprising from 5 to 12 atoms, not counting the hydrogen atoms, and incorporating in its carbon skeleton one, two or three hetero atoms chosen from nitrogen, oxygen or sulfur, the term substituted associated with the expressions aryl, arylalkyl, diarylalkyl, heteroaryl and heteroarylalkyl meaning that the aryl or heteroaryl ring-system or -systems can be substituted with one or more linear or branched lower alkyl group(s) having 1 to 6 carbon atoms, linear or branched lower alkoxy group(s) having 1 to 6 carbon atoms or hydroxyl, nitro, halogen or trifluoromethyl group(s).

The invention also encompasses the process for obtaining the compounds of general formula (I), wherein a 3-amino-2-pyridinone of general formula (II):

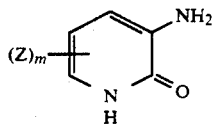
(II)

in which Z and m have the same meaning as in the compounds of general formula (I), is reacted in solution at −78° C. (the temperature of an acetone/dry ice mixture) in an aprotic solvent or mixture of aprotic solvents with bis(trichloromethyl) carbonate (triphosgene) in the presence of a basic amine such as, for example, triethylamine so as to obtain a 1H-oxazolo[5,4-b]pyridin-2-one of general formula (III):

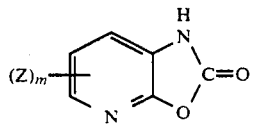
(III)

in which Z and m have the same meaning as in the compounds of general formula (I), which is reacted with an alkali metal alcoholate or hydride in an aprotic organic medium so as to obtain the compound of general formula (IV):

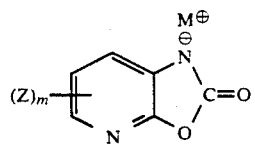
(IV)

in which Z and m have the same meaning as in the compounds of general formula (I) and M represents an alkali metal, which is reacted in an organic medium and at a temperature between room temperature and the refluxing temperature of the chosen solvent (or solvent mixture):

a) either with an electrophilic compound (preferably in excess) of general formula (V):

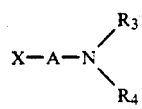
(V)

in which X represents a halogen atom and A, $R_3$ and $R_4$ have the same meaning as in the compounds of general formula (I), so as to obtain, after cooling, extraction and, where appropriate, purification, the compounds of general formula ($I_A$):

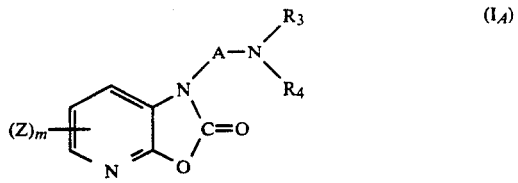
($I_A$)

a special case of the compounds of general formula (I) for which $R_1$ and $R_2$, with the oxygen and the nitrogen which carry them, form an

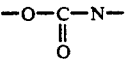

link, Z, m, A, $R_3$ and $R_4$ having the same meaning as in the compounds of general formula (I), b) or with an electrophilic compound (preferably in excess) of general formula (VI):

X—A—X'  (VI)

in which X and X', which may be identical or different, each represent a halogen atom, so as to obtain the halogenated compound of general formula (VII):

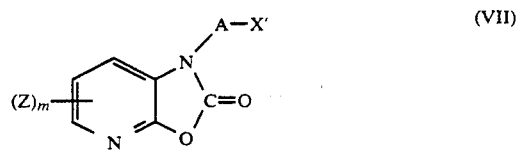
(VII)

in which X', A, Z and m have the same meaning as above, which is finally reacted with an amine (preferably in excess) of general formula (VIII):

(VIII)

in which $R_3$ and $R_4$ have the same meaning as in the compounds of formula (I), in an organic medium, optionally in the presence of a basic amine such as, for example, diisopropylamine and at a temperature between room temperature and the refluxing temperature of the chosen solvent, so as to obtain, after cooling, extraction and, where appropriate, purification, the compounds of general formula ($I_A$), c) or, in the special case of the compounds of general formula ($I_A$) in which A is a methylene link —CH$_2$—, with chloromethyl phenyl sulfide so as to obtain the compounds of general formula (IX):

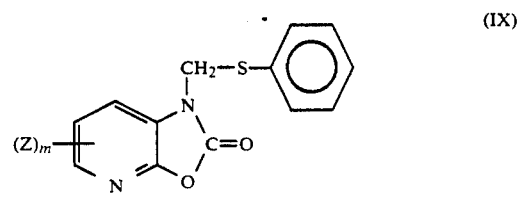
(IX)

in which Z and m have the same meaning as in the compounds of general formula (I), which is then reacted in an organic medium with sulfuryl chloride to obtain, after purification, the chlorinated compound of general formula (X):

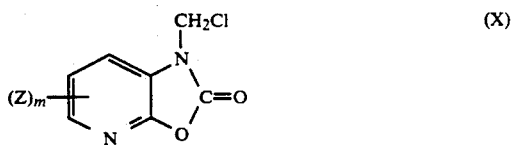

in which Z and m have the same meaning as in the compounds of general formula (I), which is then reacted as above with compounds of general formula (VIII) so as to obtain the compounds of general formula ($I_A$) with A being a methylene link —$CH_2$—.

The compounds of general formula ($I_A$) for which A is a methylene link —$CH_2$— may also be obtained in a single step by condensation in a lower aliphatic alcohol medium of a compound of general formula (III), an amine of general formula (VIII) in slight excess and an excess of formaldehyde at a temperature between room temperature and the refluxing temperature of the reaction medium, followed, after cooling and isolation, by an optional purification by chromatography on a silica column.

The compounds ($I_A$) obtained by the methods mentioned above can, if so desired, be separated into their isomers and/or salified with a pharmaceutically acceptable acid.

The compounds ($I_A$) can also, if so desired, be treated with an alkaline agent such as, for example, sodium hydroxide in aqueous solution at a temperature between room temperature and the refluxing temperature of the reaction medium to yield, after, where appropriate, acidification and/or neutralization of the reaction medium, the compounds of general formula ($I_B$):

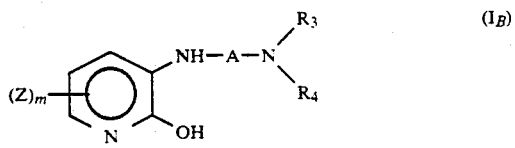

a special case of the compounds of general formula (I) for which $R_1 = R_2 = H$, and A, $R_3$, $R_4$, Z and m having the same meaning as in the compounds of general formula (I).

A pharmacological study of the compounds of the invention showed that they were of low toxicity, endowed with a high, pure analgesic activity and hence devoid of the drawbacks inherent in the antiinflammatory component of non-morphinic compounds exhibiting this type of activity (ulcerogenic action, interference with coagulation processes, etc.).

This pure analgesic activity renders the compounds of the present invention very advantageous in numerous indications such as rheumatic pain, lumbosciatic neuralgia, cervicobrachial neuralgia, pain associated with trauma such as sprains, fractures, dislocations, posttraumatic pain, postoperative pain, dental pain, neurological pain such as facial neuralgia, visceral pain such as nephritic colic, dysmenorrhea, proctological surgery, pain in the ENT region, pancreatitis, various pains, headache, cancer pain, etc.

The subject of the present invention is also pharmaceutical compositions containing the products of formula (I) or one of their addition salts with a pharmaceutically acceptable acid, alone or in combination with one or more pharmaceutically acceptable, non-toxic, inert excipients or vehicles.

Among the pharmaceutical compositions according to the invention, there may be mentioned, more especially, those which are suitable for oral, parenteral, nasal, rectal, perlingual, ocular or respiratory administration, and in particular injections, aerosols, eye or nasal drops, simple or sugar-coated tablets, sublingual tablets, sachets, packets, hard gelatin capsules, sublingual preparations, troches, suppositories, creams, ointments, skin gels, and the like.

The appropriate dosage varies according to the patient's age and weight, the administration route and the nature of the therapeutic indication and of any associated treatments, and lies between 10 mg and 4 grams per 24 hours.

The examples which follow illustrate the invention and in no way limit it.

EXAMPLE 1

1-[2-(4-PHENYL-1-PIPERAZINYL)ETHYL]-1H-OXAZOLO[5,4-b]PYRIDIN-2-ONE

STAGE A: 1H-OXAZOLO[5,4-b]PYRIDIN-2-ONE

A solution of 0.33 g (3 mmol) of 3-amino-2-hydroxypyridine in a 50:50 mixture of dichloromethane and anhydrous tetrahydrofuran is cooled to $-78°$ C. (the temperature of an acetone/dry ice mixture) under an inert atmosphere (argon). 2.2 $cm^3$ (15 mmol) of triethylamine are added, and 0.98 g (3.3 mmol) of bis(trichloromethyl) carbonate (triphosgene) dissolved in 10 $cm^3$ of a 50:50 mixture of dichloromethane and tetrahydrofuran is then run in dropwise.

After 30 minutes' stirring, a further 2.2 $cm^3$ (15 mmol) of triethylamine are added and stirring is maintained for six hours.

After evaporation of the solvent under reduced pressure, the crystals obtained are purified by flash chromatography on a silica column (eluent:ethyl ether/tetrahydrofuran, 50:50).

1H-Oxazolo[5,4-b]pyridin-2-one is finally obtained in a 78% yield.

Melting point: 252° C.

IR (KBr disk) 3220 $cm^{-1}$ (weak) ν NH, 2900–3000 $cm^{-1}$ ν CH, 1775 $cm^{-1}$ ν C=O.

$^1$H NMR (CDCl$_3$, TMS): δ: 11.8 ppm, 1H, singlet NH, δ: 7.92 ppm, 1H, doublet of doublet (J=5 Hz and J=1.5 Hz) H (5), δ: 7.46 ppm, 1H, doublet of doublet (J=8 Hz and J=1.5 Hz) H (7), δ: 7.17 ppm, 1H, doublet of doublet (J=8 Hz and J=5 Hz) H (6).

METHOD A

STAGE B: 1-(2-BROMOETHYL)-1H-OXAZOLO[5,4-b]PYRIDIN-2-ONE 1.36 g (10 mmol) of 1H-oxazolo[5,4-b]pyridin-2-one are dissolved in 80 $cm^3$ of dimethylformamide under an inert atmosphere (argon). 15 mmol of sodium hydride, washed beforehand with tetrahydrofuran, are then added at room temperature and in small portions.

The mixture is heated to 50° C. for 40 minutes and then cooled to room temperature, and 5.17 $cm^3$ (60 mmol) of dibromoethane diluted in 20 $cm^3$ of dimethylformamide are added.

The mixture is heated to 110° C. for one hour and the dimethylformamide is then removed by distillation under reduced pressure.

The residue is taken up with water, the aqueous phase is extracted with methylene chloride, the organic phases are dried over magnesium sulfate and then taken to dryness and the crude product is purified by flash chromatography on a silica column (230–240 mesh silica; eluent: acetonitrile/methylene chloride, 5:95).

1-(2-Bromoethyl)-1H-oxazolo[5,4-b]pyridin-2-one is finally obtained in a 66% yield.

Melting point: 109°–110° C.

IR (KBr disk): 2900–3000 cm$^{-1}$ ν CH. 1760 cm$^{-1}$ ν C=0.

$^1$H NMR (CDCl$_3$, TMS): δ: 8.7 ppm, 1H, doublet of doublet (J=5.1 Hz and J=1.5 Hz) H (5), δ: 7.37 ppm, 1H, doublet of doublet (J=7.7 Hz and J=1.5 Hz) H (7), δ: 7.17 ppm, 1H, doublet of doublet (J=5.1 Hz and J=7.7 Hz) H (6), δ: 4.27 ppm, 2H, triplet (J=6.3 Hz) CH$_2$—N, δ: 3.7 ppm, 2H, triplet (J=6.3 Hz) CH$_2$.

STAGE C: 1-[2-(4-PHENYL-1-PIPERAZINYL)E-THYL]-1H-OXAZOLO[5,4-b]PYRIDIN-2-ONE

In a round-bottomed flask under an argon atmosphere, surmounted by a condenser, 2.43 g (15 mmol) of 1-phenylpiperazine and then 2.61 cm$^3$ (15 mmol) of diiso-propylethylamine are added to a solution of 2.43 g (10 mmol) of 1-(2-bromoethyl)-1H-oxazolo]5,4-b]pyridin-2-one in acetonitrile.

The mixture is brought to 80° C. for 12 hours and then allowed to cool, and the acetonitrile is evaporated off under reduced pressure.

The residue is taken up in water, the alkalinity of the medium is checked, the aqueous phase is extracted with methylene chloride and the methylene chloride phases are dried over magnesium sulfate and taken to dryness.

The crude product obtained is then purified by chromatography on a silica column (230–240 mesh silica; eluent:methylene chloride/methanol, 95:5).

1-[2-(4-Phenyl-1-piperazinyl)ethyl]-1H-oxazolo-[5,4-b]pyridin-2-one is finally obtained in a 90% yield.

Melting point: 182°–183° C.

IR (KBr disk) 2900–3100 cm$^{-1}$ ν CH, 1760 cm$^{-1}$ ν C=0.

$^1$H NMR (CDCl$_3$, TMS): δ: 8.03 ppm, 1H, doublet of doublet (J=5 Hz and J=1.3 Hz) H (5), δ: 7.3 ppm, 1H, doublet of doublet (J=7.6 Hz and J=1.3 Hz) H (7), δ: 7.25 ppm, 2H, doublet, aromatic H, δ: 7.13 ppm, 1H, doublet of doublet (J=5 Hz and J=7.6 Hz) H (6), δ: 4 ppm, 2H, triplet (J=6 Hz) CH$_2$—N, δ: 3.15 ppm, 4H, multiplet, piperazine H, δ: 2.77 ppm, 2H, triplet (J=6 Hz) CH$_2$, δ: 2.68 ppm, 4H, multiplet, piperazine H.

METHOD B

STAGE B: 4-PHENYL-1-(2-CHLOROETHYL)-PIPERAZINE 6.49 g (40 mmol) of 1-phenylpiperazine are dissolved under argon in 40 cm$^3$ of dimethylformamide, and 6.63 g (48 mmol) of anhydrous potassium carbonate and then 6.88 g (48 mmol) of 1-bromo-2-chloroethane are added.

The mixture is stirred at room temperature for 22 hours and the insoluble inorganic matter is then removed by filtration.

The filtrate is acidified with ethanol saturated with dry hydrochloric acid to pH 1.

400 cm$^3$ of anhydrous ethyl ether are added and the 4-phenyl-1-(2-chloroethyl)piperazine, which precipitates in the medium, is isolated by taking to dryness.

The hydrochloride is taken up in 10% aqueous sodium carbonate solution and the aqueous phase is then extracted with methylene chloride.

The organic phase is dried over magnesium sulfate, filtered and then taken to dryness under reduced pressure.

The 4-phenyl-1-(2-chloroethyl)piperazine obtained is employed in the next step without further treatment.

STAGE C: 1-[2-(4-PHENYL-1-PIPERAZINYL)E-THYL]-1H-OXAZOLO[5,4-b]PYRIDIN-2-ONE 15 mmol of sodium hydride, washed beforehand with THF, are added in small portions to a solution, under an argon atmosphere, of 1.36 g (10 mmol) of 1H-oxazolo[5,4-b]pyridin-2-one in 80 cm$^3$ of dimethylformamide.

The mixture is heated to 50° C. for 40 minutes and then cooled, and 12 mmol of 4-phenyl-1-(2-chloroethyl)-piperazine dissolved in 20 cm$^3$ of dimethylformamide are added at room temperature.

The mixture is brought to reflux (≃153° C.) for 90 minutes. The residue is taken up with water, the aqueous phase is extracted with methylene chloride and the methylene chloride phases are dried over magnesium sulfate and taken to dryness.

The crude product obtained is then purified on a silica column (230–240 mesh silica; eluent:methylene chloride/methanol, 95:5).

1-[2-(4-Phenyl-1-piperazinyl)ethyl]-1H-oxazolo-[5,4-b]pyridin-2-one is obtained in a 64% yield.

EXAMPLE 2

1-{2-[4-(3-TRIFLUOROMETHYLPHENYL)-1-PIPERAZINYL]ETHYL}-1H-OXAZOLO[5,4-b]PYRIDIN-2-ONE

Both methods of synthesis described in Example 1 may be used, replacing 1-phenylpiperazine by 1-(3-trifluoromethylphenyl)piperazine.

Melting point: 99°–100° C.

IR (KBr disk): 2700–3000 cm$^{-1}$ ν CH. 1765 cm$^{-1}$ ν C=0.

$^1$H NMR (CDCl$_3$, TMS): δ: 8.03 ppm, 1H, doublet of doublet (J=5.4 Hz and J=1.3 Hz) H(5), δ: 7.3 ppm, 3H, multiplet H (7)+aromatic 2H, δ: 7.14 ppm, 1H, doublet of doublet (J=7.3 Hz and J=5.4 Hz) H(6), δ: 7.0–7.08 ppm, 2H, multiplet, aromatic 2H, δ: 3.98 ppm, 2H, triplet (J=6.3 Hz) N—CH$_2$, δ: 3.16 ppm, 4H, multiplet, piperazine 2 CH$_2$, δ: 2.78 ppm, 2H, triplet (J=6.3 Hz) CH$_2$, δ: 2.67 ppm, 4H, multiplet, piperazine 2 CH$_2$.

EXAMPLE 3

1-(2-MORPHOLINOETHYL)-1H-OXAZOLO-[5,4-b]PYRIDIN-2-ONE

Both methods of synthesis described in Example 1 may be used, replacing 1-phenylpiperazine by morpholine.

Melting point: 102°–103° C.

IR (KBr disk) 2700–3000 cm$^{-1}$ ν CH.

$^1$H NMR (CDCl$_3$, TMS): δ: 8.06 ppm, 1H, doublet of doublet (J=5 Hz and J=1.4 Hz) H(5), δ: 7.27 ppm, 1H, doublet of doublet (J=7.9 Hz and J=1.4 Hz) H(7), δ: 7.14 ppm, 1H, doublet of doublet (J=7.9 Hz and J=5 Hz) H (6), δ: 3.93 ppm, 2H, triplet (J=6.2 Hz( CH$_2$, δ: 3.63 ppm, 4H, multiplet, morpholine 2CH$_2$, δ: 2.49 ppm, 4H, multiplet, morpholine 2 CH$_2$.

EXAMPLE 4

1-{2-[4-(4-FLUOROPHENYL)-1-PIPERAZINYL]ETHYL}-1H-OXAZOLO[5,4-b]PYRIDIN-2-ONE

Both methods of synthesis described in Example 1 may be used, replacing 1-phenylpiperazine by 1-(4-fluoro-phenyl)piperazine.

Melting point: 135° C.

IR (KBr disk) 3100-2800 cm$^{-1}$ v CH. 1760 cm$^{-1}$ v C=0.

$^1$H NMR (CDCl$_3$, TMS): δ: 8.04 ppm, 1H, doublet of doublet (J=5.1 Hz and J=1.6 Hz) H (5), δ: 7.3 ppm, 1H, doublet of doublet (J=7.5 Hz and J=1.6 Hz) H (7), δ: 7.14 ppm, 1H, doublet of doublet (J=7.5 Hz and J=5.1 Hz) H (6), δ: 6.8-6.99 ppm, 4H, multiplet, aromatic H, δ: 3.98 ppm, 2H, triplet (J=6.1 Hz) CH$_2$, δ: 3.03-3.08 ppm, 4H, multiplet, piperazine CH$_2$, δ: 2.78 ppm, 2H, triplet, (J=6.1 Hz) CH$_2$, δ: 2.66-2.72 ppm, 4H, multiplet, piperazine CH$_2$.

EXAMPLE 5

1-{2-[4-(2-METHOXYPHENYL)-1-PIPERAZINYL]ETHYL}-1H-OXAZOLO[5,4-b]PYRIDIN-2-ONE

Both methods of synthesis described in Example 1 may be used, replacing 1-phenylpiperazine by 1-(2-methoxyphenyl)piperazine.

Melting point: 146° C.

IR (KBr disk) 3100-2725 cm$^{-1}$ v CH, 1770 cm$^{-1}$ v C=0.

$^1$H NMR (CDCl$_3$, TMS): δ: 8.03 ppm, 1H, doublet of doublet (J=5.1 Hz and J=1.2 Hz) H (5), δ: 7.32 ppm, 1H, doublet of doublet (J=7.5 Hz and J=1.2 Hz) H(7), δ: 7.14 ppm, 1H, doublet of doublet (J=7.5 Hz and J=5.3 Hz) H (6), δ: 6.84-7.03 ppm, 5H, multiplet, aromatic H, δ: 3.99 ppm, 2H, triplet (J=6.3 Hz) CH$_2$, δ: 3.86 ppm, 3H, singlet OCH$_3$, δ: 2.99-3.08 ppm, 4H, multiplet, piperazine CH$_2$, δ: 2.79 ppm, 2H, triplet, (J=6.3 Hz) CH$_2$, δ: 2.69-2.75 ppm, 4H, multiplet, piperazine CH$_2$.

EXAMPLE 6

1-[2-(4-PHENYL-1-PIPERIDYL)ETHYL]-1H-OXAZOLO[5,4-b]PYRIDIN-2-ONE

Both methods of synthesis described in Example 1 may be used, replacing 1-phenylpiperazine by 4-phenylpiperidine.

Melting point: 128° C.

IR (KBr disk) 3100-2725 cm$^{-1}$ v CH. 1760 cm$^{-1}$ v C=0.

$^1$H NMR (CDCl$_3$, TMS): δ: 8.04 ppm, 1H, doublet of doublet (J=5.1 Hz and J=1.6 Hz) H (5), δ: 7.10-7.34 ppm, 7H, multiplet H (6), H(7) and 5 aromatic H, δ: 3.98 ppm, 2H, triplet (J=6.3 Hz) CH$_2$, δ: 3.01-3.08 ppm, 2H, multiplet, piperidine CH$_2$, δ: 2.75 ppm, 2H, triplet, (J=6.3 Hz) CH$_2$, δ: 2.44-2.55 ppm, 1H, multiplet, piperidine CH, δ: 2.13-2.26 ppm, 2H, multiplet, piperidine CH$_2$, δ: 1.60-1.88 ppm, 4H, multiplet piperidine CH$_2$.

EXAMPLE 7

1-[2-(1-PYRROLIDINYL)ETHYL]-1H-OXAZOLO[5,4-b]PYRIDIN-2-ONE

Both methods of synthesis described in Example 1 may be used, replacing 1-phenylpiperazine by pyrrolidine.

Melting point: 90°-91° C.

IR (KBr disk) 3080-2700 cm$^{-1}$ v CH, 1750 cm$^{-1}$ v C=0.

$^1$H NMR (CDCl$_3$, TMS): δ: 8.02 ppm, 1H, doublet of doublet (J=5.1 Hz and J=1.4 Hz) H (5), δ: 7.29 ppm, 1H, doublet of doublet (J=7.5 Hz and J=1.4 Hz) H(7), δ: 7.12 ppm, 1H, doublet of doublet (J=7.5 Hz and J=5.1 Hz) H(6), δ: 3.96 ppm, 2H, triplet (J=6.3 Hz) CH$_2$, δ: 2.84 ppm, 2H, triplet, (J=6.3 Hz) CH$_2$, δ: 2.54-2.62 ppm, 4H, multiplet, pyrrolidine CH$_2$, δ: 1.73-1.81 ppm, 4H, multiplet, pyrrolidine CH$_2$.

EXAMPLE 8

1-[2-(HEXAMETHYLENIMINO)ETHYL]-1H-OXAZOLO[5,4-b]PYRIDIN-2-ONE

Both methods of synthesis described in Example 1 may be used, replacing 1-phenylpiperazine by hexamethylenimine.

Melting point: 86° C.

IR (KBr disk) 3080-2700 cm$^{-1}$ v CH, 1750 cm$^{-1}$ v C=0.

$^1$H NMR (CDCl$_3$, TMS): δ: 8.02 ppm, 1H, doublet of doublet (J=5.2 Hz and J=1.3 Hz) H (5), δ: 7.31 ppm, 1H, doublet of doublet (J=7.8 Hz and J=1.3 Hz) H(7), δ: 7.14 ppm, 1H, doublet of doublet (J=7.8 Hz and J=5.2 Hz) H (6), δ: 3.89 ppm, 2H, triplet (J=6.5 Hz) CH$_2$, δ: 2.87 ppm, 2H, triplet, (J=6.5 Hz) CH$_2$, δ: 2.64-2.72 ppm, 4H, multiplet CH$_2$, δ: 1.50-1.65 ppm, 8H, multiplet CH$_2$.

EXAMPLE 9

1-(3-MORPHOLINO-1-PROPYL)-1H-OXAZOLO-[5,4-b]PYRIDIN-2-ONE

STAGE A: 1-(3-BROMOPROPYL)-1H-OXAZOLO[5,4-b]PYRIDIN-2-ONE

The procedure is as for 1-(2-bromoethyl)-1H-oxazolo[5,4-b]pyridin-2-one (Example 1, Method A, stage B), replacing 1,2-dibromoethane by 1,3-dibromopropane.

1-(3-Bromopropyl)-1H-oxazolo[5,4-b]pyridin-2-one is obtained in a 57% yield.

Melting point: 62°-63° C.

IR (KBr disk) 2900-3100 cm$^{-1}$ v CH, 1760 cm$^{-1}$ v C=0.

$^1$H NMR (CDCl$_3$, TMS): δ: 8 ppm, 1H, doublet of doublet (J=5.2 Hz and J=1.4 Hz) H (5), δ: 7.38 ppm, 1H, doublet of doublet (J=8 Hz and J=1.4 Hz) H (7), δ: 7.17 ppm, 1H, doublet of doublet (J=5.2 Hz and J=8 Hz) H (6), δ: 4 ppm, 2H, triplet (J=6.3 Hz) CH$_2$N, δ: 3.45 ppm, 2H, triplet (J=6.3 Hz) CH$_2$, δ: 2.37 ppm, 2H, multiplet CH$_2$.

STAGE B: 1-(3-MORPHOLINO-1-PROPYL)-1H-OXAZOLO-]5,4-b]PYRIDIN-2-ONE

The procedure is as for 1-[2-(4-phenyl-1-piperazinyl)ethyl]-1H-oxazolo[5,4-b]pyridin-2-one (Example 1, Method A, stage C), replacing 1-(2-bromoethyl)-1H-oxazolo[5,4-b]pyridin-2-one by 1-(3-bromopropyl)-1H-oxazolo[5,4-b]pyridin-2-one and 1-phenylpiperazine by morpholine.

Yield: 72%.

Melting point: 170°-171° C.

IR (KBr disk) 2700-3100 cm$^{-1}$ v CH, 1760 cm$^{-1}$ v C=0.

$^1$H NMR (CDCl$_3$, TMS): δ: 8.04 ppm, 1H, doublet of doublet (J=5.2 Hz and J=1.5 Hz) H(5), δ: 7.32 ppm, 1H, doublet of doublet (J=7.4 Hz and J=1.5 Hz) H(7), δ: 7.14 ppm, 1H, doublet of doublet (J=7.4 Hz and J=5.2 Hz) H(6), δ: 3.95 ppm, 2H, triplet (J=6.6 Hz)

CH$_2$, δ: 3.62 ppm, 4H, multiplet, morpholine 2 CH$_2$, δ: 2.4 ppm, 2H, triplet (J=6.6 Hz) CH$_2$, δ: 2.35 ppm, 4H, multiplet, morpholine 2 CH$_2$, δ: 1.96 ppm, 2H, multiplet CH$_2$.

EXAMPLE 10

1-[3-(4-PHENYL-1-PIPERAZINYL)-1-PROPYL]-1H-OXAZOLO[5,4-b]PYRIDIN-2-ONE

The procedure is as for 1-(3-morpholinopropyl)-1H-oxazolo[5,4-b]pyridin-2-one, replacing morpholine in stage B by 1-phenylpiperazine.

Melting point: 119° C.

IR (KBr disk) 3100–2760 cm$^{-1}$ ν CH. 1760 cm$^{-1}$ ν C=O.

$^1$H NMR (CDCl$_3$, TMS): δ: 8.02 ppm, 1H, doublet of doublet (J=5.1 Hz and J=1.6 Hz) H (5), δ: 7.26 ppm, 2H, triplet (J=7.9 Hz) aromatic H, δ: 7.12 ppm, 1H, doublet of doublet (J=7.9 Hz and J=5.1 Hz) H (6), δ: 6.91 ppm, 2H, doublet (J=7.9 Hz) aromatic H, δ: 6.85 ppm, 1H, triplet (J=7.9 Hz) aromatic H, δ: 3.96 ppm, 2H, triplet (J=6.7 Hz) CH$_2$, δ: 3.09–3.16 ppm, 4H, multiplet piperazine CH$_2$, δ: 2.5–2.55 ppm, 4H, multiplet piperazine CH$_2$, δ: 2.45 ppm, 2H, triplet (J=6.7 Hz) CH$_2$, δ: 2.00 ppm, 2H, quadruplet (J=6.7 Hz) CH$_2$.

EXAMPLE 11

1-(4-MORPHOLINO-1-n-BUTYL)-1H-OXAZOLO[5,4-b]PYRIDIN-2-ONE

STAGE A: 1-(4-BROMOBUTYL)-1H-OXAZOLO[5,4-b]-PYRIDIN-2-ONE

The procedure is as for 1-(2-bromoethyl)-1H-oxazolo[5,4-b]pyridin-2-one (Example 1, Method A, stage B), replacing 1,2-dibromoethane by 1,4-dibromobutane.

Yield: 62%.

Melting point: 60°–61° C.

IR (KBr disk) 2900–3100 cm$^{-1}$ ν CH. 1760 cm$^{-1}$ ν C=O.

$^1$H NMR (CDCl$_3$, TMS): δ: 8.05 ppm, 1H, doublet of doublet (J=5.1 Hz and J=1.5 Hz) H (5), δ: 7.28 ppm, 1H, doublet of doublet (J=7.9 Hz and J=1.5 Hz) H (7), δ: 7.16 ppm, 1H, doublet of doublet (J=7.9 Hz and J=5.1 Hz) H (6), δ: 3.9 ppm, 2H, triplet (J=6.5 Hz) CH$_2$, δ: 3.46 ppm, 2H, triplet (J=5.9 Hz) CH$_2$.

STAGE B: 1-(4-MORPHOLINO-1-n-BUTYL)-1H-OXAZOLO-[5,4-b]PYRIDIN-2-ONE

The procedure is as for 1-2-(4-phenyl-1-piperazinyl)ethyl]-1H-oxazolo[5,4-b]pyridin-2-one (Example 1, Method A, stage C), replacing 1-(2-bromoethyl)-1H-oxazolo[5,4-b]pyridin-2-one by 1-(4-bromobutyl)-1H-oxazolo[5,4-b]pyridin-2-one and 1-phenylpiperazine by morpholine.

Yield: 76%.

Melting point: 108°–109° C.

IR (KBr disk) 2700–3000 cm$^{-1}$ ν CH. 1760 cm$^{-1}$ ν C=O.

$^1$H NMR (CDCl$_3$, TMS): δ: 8.02 ppm, 1H, doublet of doublet (J=5.2 Hz and J=1.5 Hz) H (5), δ: 7.25 ppm, 1H, doublet of doublet (J=7.4 Hz and J=1.5 Hz) H (7), δ: 7.14 ppm, 1H, doublet of doublet (J=7.4 Hz and J=5.2 Hz) H (6), δ: 3.88 ppm, 2H, triplet (J=7.1 Hz) CH$_2$, δ: 3.7 ppm, 2H, multiplet, morpholine 2H, δ: 0.43–2.46 ppm, 4H, multiplet, morpholine CH$_2$+2H, δ: 1.84 ppm, 2H, multiplet, morpholine 2H.

EXAMPLE 12

1-[4-(4-PHENYL-1-PIPERAZINYL)-1-n-BUTYL]-1H-OXAZOLO[5,4-b]PYRIDIN-2-ONE

The procedure is as for 1-(4-morpholino-1-n-butyl)-1H-oxazolo[5,4-b]pyridin-2-one, replacing morpholine in stage B by 1-phenylpiperazine.

Melting point: 94° C.

IR (KBr disk) 2960–2760 cm$^{-1}$ ν CH. 1765 cm$^{-1}$ ν C=O.

$^1$H NMR (CDCl$_3$, TMS): δ: 8.03 ppm, 1H, doublet of doublet (J=5.1 Hz and J=1.4 Hz) H (5), δ: 7.21 ppm, 3H, multiplet H (7) and aromatic 2H, δ: 7.15 ppm, 1H, doublet of doublet (J=7.9 Hz and J=5.1 Hz) H (6), δ: 6.92 ppm, 2H, doublet (J=7.5 Hz) aromatic H, δ: 6.84 ppm, 1H, triplet (J=7.5 Hz) aromatic H, δ: 3.88 ppm, 2H, triplet (J=7.5 Hz) CH$_2$, δ: 3.16–3.22 ppm, 4H, multiplet piperazine CH$_2$, δ: 2.54–2.61 ppm, 4H, multiplet piperazine CH$_2$, δ: 2.46 ppm, 2H, triplet (J=7.5 Hz) CH$_2$, δ: 1.80–1.92 ppm, 2H, multiplet CH$_2$, δ: 1.56–1.69 ppm, 2H, multiplet CH$_2$.

EXAMPLE 13

1-{2-[4-(N,N-DIETHYLAMINOCARBONYL)-1-PIPERAZINYL]ETHYL}-1H-OXAZOLO[5,4-b]PYRIDIN-2-ONE

Both methods of synthesis described in Example 1 may be used, replacing 1-phenylpiperazine by 1-(N,N-diethyl aminocarbonyl) piperazine.

Melting point: 137° C.

IR (KBr disk) 3100–2800 cm$^{-1}$ ν CH. 1765 cm$^{-1}$ ν C=O.

$^1$H NMR (CDCl$_3$, TMS): δ: 8.02 ppm, 1H, doublet of doublet (J=5.2 Hz and J=1.3 Hz) H (5), δ: 7.27 ppm, 1H, doublet of doublet (J=7.8 Hz and J=1.3 Hz) H (7), δ: 7.12 ppm, 1H, doublet of doublet (J=7.8 Hz and J=5.2 Hz) H (6), δ: 3.94 ppm, 2H, triplet (J=2.3 Hz) CH$_2$, δ: 3.12 and 3.33 ppm, 8H, multiplet CH$_2$, δ: 2.71 ppm, 2H, triplet (J=2.3 Hz) CH$_2$, δ: 2.5 ppm, 4H, triplet (J=1.7 Hz) piperazine CH$_2$, δ: 1.10 ppm, 6H, triplet (J=5.3 Hz) CH$_3$.

EXAMPLE 14

3-[2-(4-PHENYL-1-PIPERAZINYL)ETHYL-AMINO]-2-HYDROXYPYRIDINE

A solution of 1 mol of 1-[2-(4-phenyl-1-piperazinyl)ethyl]-1H-oxazolo[5,4-b]pyridin-2-one (obtained in Example 1) in 50 cm$^3$ of 10% aqueous sodium hydroxide solution is heated to reflux for 4 hours.

After cooling, the aqueous solution is slightly acidified by adding 30% aqueous hydrochloric acid and then neutralized to pH 7 with saturated aqueous sodium bicarbonate solution.

The precipitate obtained is filtered off, washed three times with water and then dried.

PHARMACOLOGICAL STUDY OF THE COMPOUNDS OF THE INVENTION

A. TESTING FOR ANALGESIC ACTIVITY

1) Acetic acid-induced cramps: "Acetic acid writhing"

The analgesic potential of these compounds was investigated according to the so-called "acetic acid writhing" test (or alternatively "KOSTER" test), which is based on counting the abdominal cramps induced in rats by the intraperitoneal injection of acetic acid.

Male Wistar rats randomized in batches of 5 (weight 150±10 g) received the test compounds orally 30 min before the intraperitoneal injection of 1 cm³ of 1% acetic acid.

The number of cramps is counted during the 25 minutes following the injection.

The percentage activity was assessed for each compound (% decrease in the number of cramps in the treated animals relative to the controls).

2) Phenylbenzoquinone-induced cramps: "PBQ writhing"

The analgesic potential of these compounds was investigated according to the so-called "PBQ writhing" test (or alternatively "SIGMUND" test), which is based on counting the cramps induced in mice by the intraperitoneal injection of phenylbenzoquinone.

Male CD-1 mice randomized in batches of 5 received the test compounds orally 30 min before the intraperitoneal injection of 0.25 cm³ of a 0.01% solution of phenylbenzoquinone in a 95:5 water/ethanol mixture.

The number of cramps is counted between the 5th and the 15th minute after the injection of phenylbenzoquinone.

The percentage activity was assessed for each compound (% decrease in the number of cramps in the treated animals relative to the controls).

3) Results

| PRODUCT | DOSE | Acetic Acid Whrithing % inhibition | PBQ Whrithing % inhibition |
| --- | --- | --- | --- |
| Aspirin | 50 mg/kg | 69% | 70% |
| 1-[3-(4-phenyl piperazinyl)-1-propyl]-1H-oxazolo[5,4-b]pyridin-2-one | 50 mg/kg | 92% | 98% |
| 1-[4-(4-phenyl-1-piperazinyl)-1-butyl]-1H-oxazolo[5,4-b]pyridin-2-one | 50 mg/kg | 96% | 91% |
| 1-[2-(4-(4-fluoro-phenyl)-1-piperazinyl)ethyl]-1H-oxazolo-[5,4-b]pyridin-2-one | 50 mg/kg | 84% | 83% |

It is apparent that the compounds of the invention possess a very advantageous analgesic activity, which is very significantly greater than that of aspirin.

B. TESTING FOR ANTI-INFLAMMATORY ACTIVITY

The anti-inflammatory potential of the compounds was investigated on a model of acute inflammation caused by the subcutaneous injection of a colloidal suspension of carrageenan into the planter face of the rat hind foot, according to a technique base on the method of WINTER, RISLEY and NUSS Proc. Soc. Exp. Biol. Med. 111, 554 (1962) and WINEGAR et al. J. Pharmacol. Exp. Ther 166, 96 (1969).

Male Wistar SPF rats weighing 250±10 g are randomized in batches of 10 and receive the test substances orally 1 hour after the injection of 0.15 cm³ of a 1% suspension of carrageenan into the left hind foot. The inflammation is measured 5 hours later by weighing the feet, and the percentage inflammation and anti-inflammatory activity (AIA) values are calculated.

$$\% \text{ Inflammation} = \frac{\text{weight of the inflamed foot} - \text{weight of the control foot}}{\text{weight of the control foot}} \times 100$$

$$\% \text{ AIA} = \frac{\text{mean inflammation of the control batch} - \text{mean inflammation of the treated batch}}{\text{mean inflammation of the control batch}} \times 100$$

| PRODUCT | DOSE | AAI |
| --- | --- | --- |
| 1-[2-(4-phenyl-1-piperazonyl)-ethyl]-1H-oxazolo[5,4-b]pyridin-2-one | 15 mg/kg | 0% |
|  | 150 mg/kg | 12% |
|  | 250 mg/kg | 2% |
| 1-{2-[4-(3-trifluoromethylphenyl)-1-piperazinyl]ethyl}-1H-oxazol-[5,4-b]pyridin-2-one | 75 mg/kg | 0% |
|  | 200 mg/kg | 0% |
| 1-(2-morpholinoethyl)-1H-oxazolo-[5,4-b]pyridin-2-one | 100 mg/kg | 0% |
|  | 200 mg/kg | 8% |
| Glafenine | 50 mg/kg | 24% |
|  | 150 mg/kg | 28% |
| Aspirin | 150 mg/kg | 12% |

As may be observed, the anti-inflammatory activity of the compounds of the invention is very much lower than that of the reference compounds, including glafenine.

C. STUDY OF GASTRIC TOLERANCE

The gastric tolerability of these compounds was studied by testing for gastric irritation in rats according to a method based on that of LAMBLING (LAMBLING et al. Arch. Mal. Appareil digestif et nutrition (Digestive system and nutrition) (1953), 42 p 430).

The test compound are administered orally to male WISTAR SPF rats randomized in batches of 5 and subjected to a water regimen for the previous 24 hours.

After the animals have been housed in restraint cages for six hours while being deprived of drinking water, the indices of ulceration (U), of hyperemia (H) and of gastric irritation (i) are determined using the modified scoring of LWOFF (LWOFF J. M. J. Pharmacol. Paris (1971) 2 (1) p 81–83).

$$U \text{ or } H = \frac{\text{sun total of scores } (U \text{ or } H) \times \text{percentage of stomachs showing lesions}}{\text{number of animals studied}}$$

$$i = 3U + H$$

| PRODUCT | DOSE | INDEX OF GASTRIC IRRITATION |
| --- | --- | --- |
| 1-[2-(4-Phenyl-1-piperazinyl)-ethyl]-1H-oxazolo[5,4-b]-pyridin-2-one | 15 mg/kg | 8 |
|  | 75 mg/kg | 8 |
| 1-{2-[4-(3-Trifluoromethylphenyl)-1-piperazinyl]ethyl}-1H-oxazolo-[5,4-b]pyridin-2-one | 75 mg/kg | 8 |
|  | 250 mg/kg | 8 |
| 1-(2-Morpholinoethyl)-1H-oxazolo-[5,4-b]pyridin-2-one | 100 mg/kg | 0 |
|  | 250 mg/kg | 2 |
| Glafenine | 50 mg/kg | 20 |
|  | 250 mg/kg | 240 |
| Aspirin | 250 mg/kg | 146 |
| Indomethacin | 5 mg/kg | 516 |
|  | 10 mg/kg | 570 |

The compounds of the invention hence exhibit very good gastric tolerability in rats.

EXAMPLE 15

TABLETS CONTAINING 30 MG OF 1-{2-[4-(3-TRIFLUOROMETHYLPHENYL)-1-PIPERAZINYL]ETHYL}-1H-OXAZOLO[5,4-b]PYRIDIN-2-ONE

Preparation formula for 1000 tablets:

| | |
|---|---|
| 1-{2-[4-(3-Trifluoromethylphenyl)-1-piperazinyl]ethyl}-1H-oxazolo[5,4-b]pyridin-2-one | 30 g |
| Wheat starch | 15 g |
| Corn starch | 15 g |
| Lactose | 65 g |
| Magnesium stearate | 1 g |
| Silica | 1 g |
| Hydroxypropylcellulose | 2 g |

We claim:

1. A compound selected from those of formula (I):

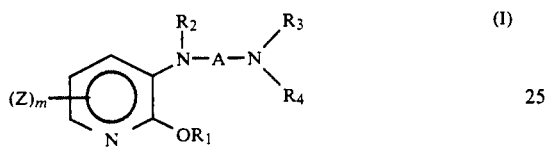

in which:

$R_1$ and $R_2$ each represent hydrogen,

Z represents halogen, linear or branched lower alkyl of 1 to 6 carbon atoms inclusive, linear or branched lower alkoxy of 1 to 6 carbon atoms inclusive or trifluoromethyl, m is 0, 1, 2, or 3, A is linear or branched alkyl of 1 to 6 carbon atoms, inclusive, $R_3$ and $R_4$, which may be identical or different, represent:

hydrogen, linear or branched lower alkyl of 2 to 6 carbon atoms, inclusive, linear or branched lower alkenyl comprising from 2 to 6 carbon atoms inclusive, optionally substituted arly optionally substituted arylalkyl in which the alkyl chain contains from 1 to 3 carbon atoms, inclusive, mono- or bicyclic cycloalkyl of 3 to 10 carbon atoms, inclusive, or alternatively:

$R_3$ and $R_4$, with the nitrogen atom to which they are linked constitute a saturated heterocyclic system selected from piperazine, piperidine, pyrrolidine, hexamethyleneimine, and morpholine, optionally substituted with one or more:

hydroxyl, oxo, linear or branched lower alkyl of 1 to 6 carbon atoms, inclusive, optionally substituted aryl, optionally substituted arylalkyl or optionally substituted diarylalkyl in which the alkyl chain contains from 1 to 3 carbon atoms, inclusive,

—CO—OR$_5$

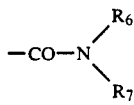

wherein $R_5$ represents:

hydrogen, linear or branched lower alkyl of 1 to 6 carbon atoms, inclusive, optionally substituted aryl, optionally substituted aralkyl in which the alkyl chain contains 1 to 3 carbon atoms, inclusive $R_6$ and $R_7$, which may be identical or different, have the same meaning as $R_5$, its isomers, optical epimers, and diastereoisomers, its addition salt with a pharmaceutically-acceptable acid and its addition salt with a pharmaceutically-acceptable base, aryl being understood to mean an aromatic, mono- or bicyclic group containing 5 to 12 carbon atoms, inclusive, the term "substituted" associated with the expressions aryl, arylalkyl, and diarylalkyl meaning that the aryl ring-system can be substituted with one or more linear or branched lower alkyl having 1 to 6 carbon atoms, inclusive linear or branched lower alkoxy having 1 to 6 carbon atoms inclusive or hydroxyl, nitro, halogen, or trifluoromethyl.

2. A compound as claimed in claim 1 for which $R_1$ and $R_2$ each represent a hydrogen atom, of formula ($I_B$):

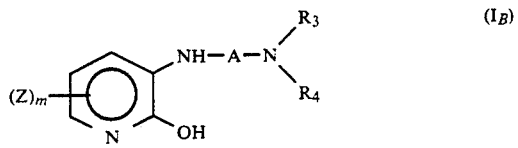

Z, m, A, $R_3$ and $R_4$ having the same meaning as in claim 1, as well as its addition salt with a pharmaceutically-acceptable acid or base.

3. A compound to claim 1 in which m=0 and A is a linear alkyl radical having 2 to 6 carbon atoms inclusive.

4. A compound as claimed in claim 1 selected from 3-[2-(4-phenyl-1-piperazinyl)ethylamino]-2-hydroxypyridine, the formula of which is shown below, and its addition salt with a pharmaceutically-acceptable acid or base.

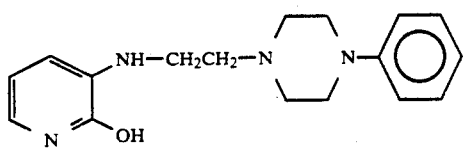

5. A method for treating a living animal or human afflicted with pain comprising the step of administering to the said living animal or human an amount of a compound of claim 1 which is effective for alleviation of said condition.

6. A pharmaceutical composition, useful for alleviating pain containing as active principle an effective amount of a compound as claimed in claim 1, in combination with a pharmaceutically-acceptable excipient or vehicle.

* * * * *

UNITED STATES PATENT AND TRADEMARK OFFICE
CERTIFICATE OF CORRECTION

PATENT NO. : 5,242,923

DATED : September 7, 1993  Page 1 of 2

INVENTOR(S) : Gérald Guillaumet, Christine Flouzat, Michelle Devissaguet, Pierre Renard, Daniel H. Caignard, Gérard Adam.

It is certified that error appears in the above-indentified patent and that said Letters Patent is hereby corrected as shown below:

Title Page, [54], line 1; insert -- COMPOUNDS -- at the end of the line.
Col. 1, line 11; insert a space after "[5,4]-".
Col. 6, line 68; "formamide" should read --Formamdide--.
Col. 7, line 27; change the "]" first instance to -- [ --.
Col. 9, line 22; change "PIPERAZINYL-" to -- PIPERAZINYL]- --.
Col. 9, line 23; delete "]" at the beginning of the line.
Col. 10, line 53; change the "]" first instance to -- [ --.
Col. 10, line 54; change "piperazinyl-" to -- piperazinyl)- --.
Col. 10, line 55; delete the ")" at the beginning of the line.
Col. 11, line 50; insert -- [ -- between "1-" and "2".
Col. 13, line 31; correct the spelling of "Writhing" in both instances.
Col. 13, line 52; correct the spelling of "plantar".
Col. 14, line 10; correct the spelling of "piperazinyl".
Col. 14, line 44; correct the spelling of "sum".
Col. 15, line 32; insert a comma after "inclusive".
Col. 15, line 41; change "2" to -- 1 --.
Col. 15, line 45; correct the spelling of "aryl".
Col. 16, line 16; delete the word "optical".
Col. 16, line 16; insert -- optical -- before "isomers".
Col. 16, line 26; insert a comma after the word "inclusive".
Col. 16, line 28; insert a comma after the word "inclusive".

UNITED STATES PATENT AND TRADEMARK OFFICE
CERTIFICATE OF CORRECTION

PATENT NO. : 5,242,923
DATED : September 7, 1993
INVENTOR(S) : Gerald Guillaumet, et al.

It is certified that error appears in the above-indentified patent and that said Letters Patent is hereby corrected as shown below:

Col. 16, line 40, change "meaning" to --meanings--.

Signed and Sealed this

Twenty-eighth Day of June, 1994

Attest:

BRUCE LEHMAN

Attesting Officer　　　Commissioner of Patents and Trademarks